(12) United States Patent
Abazajian

(10) Patent No.: US 6,518,469 B2
(45) Date of Patent: Feb. 11, 2003

(54) PROCESS FOR IMPROVED YIELDS OF HIGHER MOLECULAR WEIGHT OLEFINS FROM LOWER MOLECULAR WEIGHT OLEFINS

(76) Inventor: Armen Nazar Abazajian, 1806 Peach Brook Ct., Houston, TX (US) 77062

( * ) Notice: Subject to any disclaimer, the term of this patent is extended or adjusted under 35 U.S.C. 154(b) by 0 days.

(21) Appl. No.: 10/059,744

(22) Filed: Jan. 29, 2002

(65) Prior Publication Data

US 2002/0147374 A1 Oct. 10, 2002

Related U.S. Application Data

(63) Continuation-in-part of application No. 09/828,771, filed on Apr. 9, 2001.

(51) Int. Cl.$^7$ .............................. C07C 6/02; C07C 5/25
(52) U.S. Cl. ........................ 585/324; 585/644; 585/643; 585/664; 203/DIG. 6
(58) Field of Search ................... 585/324, 644, 585/643, 664; 203/DIG. 6

(56) References Cited

U.S. PATENT DOCUMENTS

| | | |
|---|---|---|
| 3,261,879 A | 7/1966 | Banks |
| 3,448,163 A | 6/1969 | Howman |
| 3,463,827 A | 8/1969 | Banks |
| 3,600,456 A * | 8/1971 | Bradshaw .................. 585/647 |
| 3,641,189 A | 2/1972 | Turner |
| 3,676,520 A | 7/1972 | Heckelsberg |
| 3,786,112 A | 1/1974 | Reusser |
| 4,180,524 A | 12/1979 | Reusser |
| 4,709,115 A | 11/1987 | Jung |
| 4,996,386 A | 2/1991 | Hamilton, Jr. |
| 5,043,520 A | 8/1991 | Hamilton, Jr. |
| 5,243,120 A | 9/1993 | Slaugh |

* cited by examiner

Primary Examiner—Thuan D. Dang
(74) Attorney, Agent, or Firm—Parks & Associates P.C.

(57) ABSTRACT

A process for improved yields of heavier olefins from a substantially narrow range of lighter hydrocarbon feed stock containing olefins in a reaction distillation column comprising feeding a narrow range of hydrocarbon feed stock containing olefin into a reaction distillation column at a point between its bottom and top, contacting the olefins at the point of feed with a disproportionation catalyst in alternating arrangement with an isomerization catalyst or a mixture thereof and keeping the reaction mixture in a state of vapor-liquid equilibrium for concentrating the lighter reaction products in the vapor phase and the heavier reaction products in the liquid phase by maintaining a controlled pressure and temperature profile in the reactive distillation column and for reactively creating the desired heavier molecular weight olefins over the catalysts and collecting it as bottoms product and removing the lighter molecular weight olefins overhead from the top of the reactive distillation column.

41 Claims, 4 Drawing Sheets

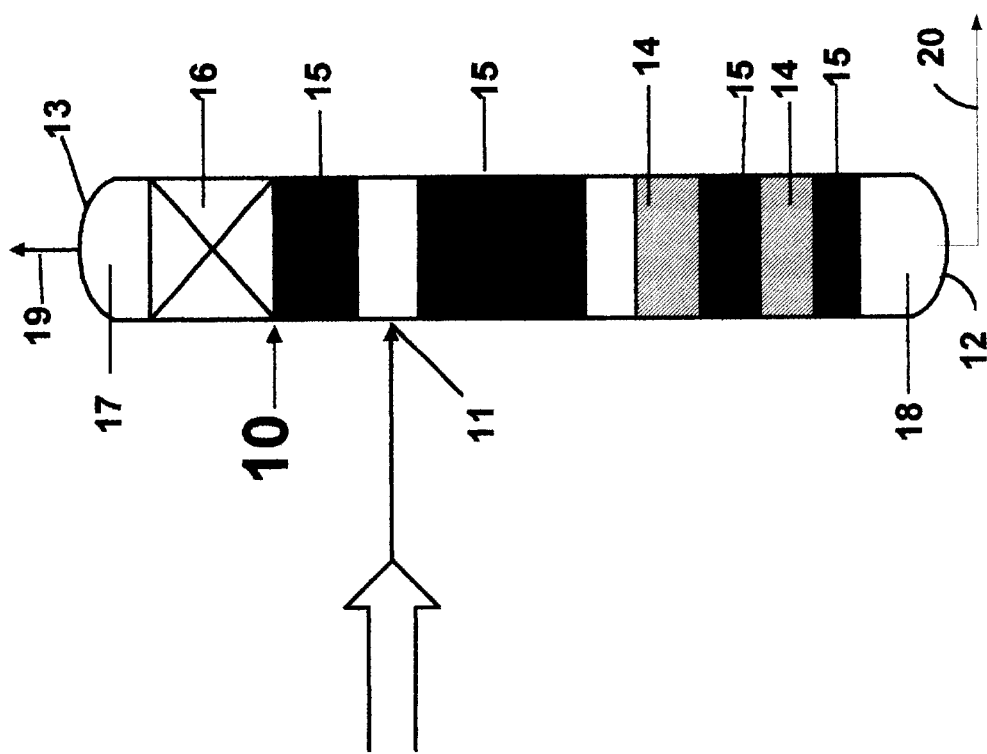

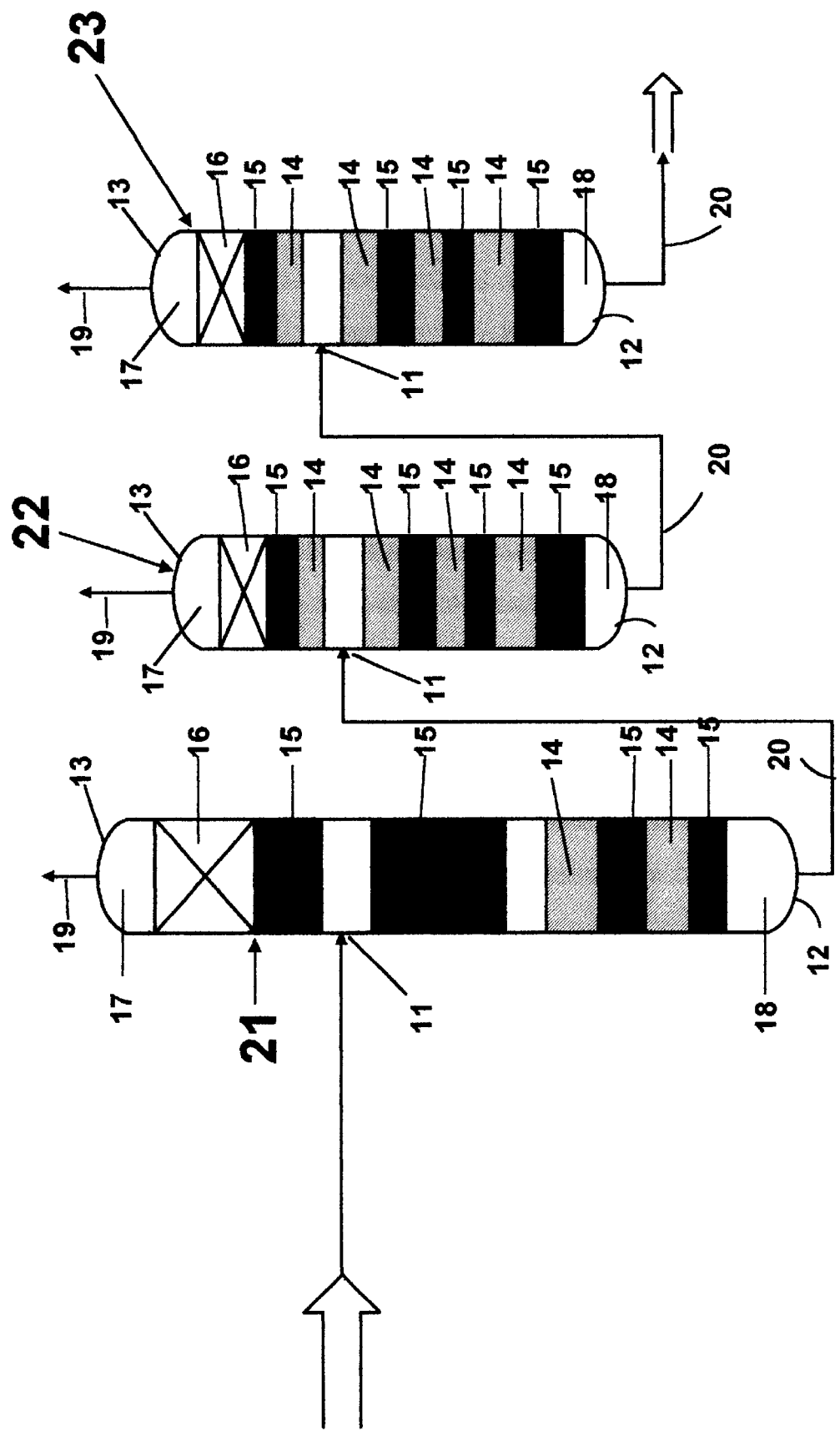
FIGURE 4: Serial Arrangement of Columns

PROCESS FOR IMPROVED YIELDS OF HIGHER MOLECULAR WEIGHT OLEFINS FROM LOWER MOLECULAR WEIGHT OLEFINS

RELATED APPLICATION

This application is a continuation-in-part of application from Ser. No. 09/828,771, filed Apr. 9, 2001.

FIELD OF INVENTION

This invention relates to a controlled process for improving the yields of heavier olefins by using a substantially narrow range of lighter olefin-containing hydrocarbon feed stock which are fed into a reaction distillation column at a predetermined point and using varying arrangements of isomerizing and disproportionating catalysts in relation to the point of feeding the narrow range of lighter olefin-containing hydrocarbon feed stock. The controlled process provides for keeping the reaction mixture in a state of vapor/liquid phase equilibrium for separating the lighter products overhead and collecting the heavier reaction products in the bottoms by maintaining controlled pressure and temperature profiles in relation to the narrow range of lighter olefin-containing hydrocarbon feed stock being used and the desired range of heavier olefin-containing hydrocarbon products desired as product in the bottoms of the reaction distillation column. Further at least one or more zones for the purpose of vapor/liquid contacting are created in the reaction distillation column for improving the separation of lighter reaction olefin products from the heavier reaction olefin products and the olefin-containing hydrocarbon feed stock and for reducing the cost of the process.

BACKGROUND OF THE INVENTION

It is well known in the prior art to use metal catalysts to react/split and recombine (disproportionate) hydrocarbon molecules, which contain olefinic or double bonds between the carbon atoms. This reaction of splitting and recombining the hydrocarbon molecules at the double bonds creates olefin hydrocarbon molecules of varying size depending on the feed stock make up and where the double bonds occurred on the feed stock molecules, but it does not necessarily give an end product with a high commercial value.

For example some of the earlier prior art reacted propylene to make ethylene and butene, or conversely make propylene from ethylene and butene in the presence of metal catalysts, which gave an olefin product but the product was not greatly different in value from the reactants. However, as these reactions are reversible, they will proceed, at most, to equilibrium, which limits the yield of the desired products. The prior art generally described only liquid phase reactions with heterogeneous catalyst in fixed beds, fluidized beds or moving beds for generally controlling approach to equilibrium of olefin-containing reactant and product mixtures.

The prior art also attempted to use other process variables like longer residence time in such systems and higher temperatures to achieve better approach to equilibrium and to shift equilibrium to a more favorable to desired products in disproportionating reactions, but they generally led to increased isomerization and other by-product reactions which were undesirable in the desired product.

Some of the prior art taught improved selectivity and conversion of reactions using 1- and 2-butene to ethylene, propylene, 2-pentene and 3-hexene by using a reactive distillation column, in the presence of a rhenium oxide as a disproportionation catalyst. In this prior art the catalysts served as a distillation substrate to facilitate a phase transfer of some of the lighter products out of the liquid phase. In this particular system the conversion and yields went up but the reaction proceeded to ethylene and propylene as the light ends and only to 2-pentene, 3-hexene as the heavy ends, which were of not much more value than the beginning feed stock used to generate them.

The prior art is replete with teaching of methods and processes for improving yields of medium-range olefins by reacting high carbon number molecule olefins with a low carbon number molecule olefins by simultaneous disproportionating and isomerizing of these olefins. In this process both the high carbon number molecule olefins and low carbon number molecule olefins are kept in a single liquid phase and the reaction process is allowed to reach near equilibrium for the formation of midrange olefins, which are detergent-range linear internal ($C_{10}$–$C_{16}$) olefin from a feedstock of light ($C_4$–$C_9$) and heavy ($C_{16}$–$C_{20}$+) alpha-olefins. Some variations of these prior art patents are even used to produce commercial linear alcohols.

These prior art patents utilized the isomerization process, which distributed the location of the double bond in the olefin molecules to make possible the production of a wider range of olefins, which readily worked if one was attempting to generate a mid-range detergent grade olefin from light and heavy alpha and internal olefins. In these been used to facilitate the isomerization of the double bonds between the carbon molecules and to create a wider range of internal olefins to be reacted to form the mid-range olefins.

Further the prior art has disclosed many processes using both an isomerization and disproportionation catalysts in a single liquid phase, elevated temperatures, and elevated pressure to attempt to achieve a desired range of products for a broad base of olefin-containing hydrocarbon feed stock, with only limited success due to limitation of equilibrium and a large range of olefin-containing hydrocarbons mixed together, which required further processing to separate the narrow desired range from both the lighter and the heavier olefin-containing hydrocarbon feed stocks and products.

The prior art further just used metal catalysts for disproportionating and isomerizing either singularly or in admixtures, but made no distinction between where these were located relative to the input of these feed stocks or which catalyst should be the first for reaction with the feed stock. The objective in the prior art was thus to make the deepest possible internal olefin of both light and heavy species before or during the disproportionation including symmetrical internal olefins. This was highly desirable when the goal was to create a mid-range olefin-containing hydrocarbon, but not for the production of heavier olefin-containing hydrocarbons from lighter olefin-containing hydrocarbons, where specifically a formation of asymmetrical olefins is desired.

OBJECTS OF THIS INVENTION

It is the object of the invention of this process to create improved yields of heavier olefins using a substantially narrow range of lighter olefin-containing hydrocarbon feed stock in a reaction distillation column containing metal catalysts and controlled temperature and pressure for reacting the narrow range of lighter olefin-containing hydrocarbon feed stock to form the improved yields of the heavier olefins. In the process of reacting the lighter olefin-containing hydrocarbon feed stock to form the improved product yields of the heavier olefins, the removal of the lighter olefin-containing hydrocarbons and other light hydrocarbons occurs.

An object of the process of this invention is to create the improved yields of heavier olefins without using high temperatures and/or longer residence time in the systems of these processes, so as to limit the formation of unwanted by-products which are undesirable in the desired product and which may interfere with the formation of the desired heavier olefins or reduce the yields thereof.

Yet a further object of the process of this invention is to shift the equilibrium of the reaction toward the formation of heavier olefin-containing hydrocarbon feed stock by reacting the lighter olefin-containing hydrocarbon feed stock with the metal catalysts and then controlling the pressure and temperature to allow the lightest unwanted olefins and other light products produced by the reaction with the metal catalysts to go into vapor phase for its removal from the reaction distillation vessel overhead.

Also an object of this process invention is to allow even the lightest olefin-containing hydrocarbon feed stocks such as 1- and 2-butene and propylene to be reacted with metal catalysts in the controlled temperatures and pressures of this process for the creation of more valuable heavier olefin-containing hydrocarbon products such as $C_5$ to $C_{10}$, which have significantly greater monetary value than the products of 2-pentene and 3-hexene.

The object of the process of this invention further allows the creation of heavier olefins from a narrow range of lighter olefin-containing hydrocarbon feed stock and then running the narrow range of heavier olefins created through another step to create yet heavier olefins.

A yet further object of this process invention is to utilize the isomerization process to adjust the location of the olefinic double bond to a predominantly asymmetrical location in the olefin molecules and then disproportionate the olefin molecules, which effectively cuts them at the double bond and recombines the asymmetrical fragments with other olefin molecules which have been disproportionated to create heavier olefin molecules and light olefin molecules and then isomerized those heavier olefin molecules and then disproportionate them again. After all disproportionation in the process the lighter undesirable olefin-containing hydrocarbons are removed in the vapor phase leaving the heavier olefins to be isomerized again before the process continues in the steps to the desired heavier olefin product.

Also an object of this invention is the use of both isomerization and disproportionation catalysts with olefin-containing hydrocarbon feed stocks and reaction products in a vapor and liquid phase in relative low temperatures and pressures to achieve a desired range of heavier olefin end products.

Further it is an object of this invention to provide at least one vapor/liquid contacting zone to facilitate the separation of the lighter olefin-containing hydrocarbons and the collection of the heavier olefins either as desired products or for further reacting in the reactive distillation column.

It is also an object of this invention to adjust the type of catalysts and where that catalysts is located as the predetermined point for the first exposure to the lighter olefin-containing hydrocarbon feedstock depending on the degree of symmetry or lack of symmetry of the olefin bonds on the lighter olefin-containing hydrocarbon feedstock which are being fed into the reactive distillation column at that predetermined point in the reactive distillation column.

Yet further and additional benefits and improvements of the process of this invention will be appreciated by other skilled in the art and those advantages and benefits of the invention will become apparent to those skilled in the art upon a reading and understanding of the following detailed description and diagrammatic drawings.

BRIEF DESCRIPTION OF THE DRAWINGS

The process of this invention may be practiced in certain physical forms and arrangements and adjustment of the variable parts herein described, but preferred embodiments of which will be described in detail in the specification and illustrated in the accompanying diagrammatic drawings which will form a part thereof.

FIG. 3 is a diagrammatic drawing of a reactive distillation column used with the process utilizing a range of lighter olefin-containing hydrocarbon feed stock of $C_3$ to $C_4$ carbon numbers being fed into the reactive distillation column at a predetermined point and with disproportionating catalyst near the predetermined feed point and isomerizing catalyst in place and in alternating arrangement with disproportionating catalyst and with at least one vapor/liquid zone created at the top of the reactive distillation column for producing C5 to C10 carbon number olefins.

FIG. 4 is a diagrammatic drawing of a series of reactive distillation columns connected together for utilizing an initial range of lighter olefin-containing hydrocarbon feed stock of $C_3$ to $C_4$ carbon numbers for producing $C_{10}$ and higher carbon number olefins by feeding the bottom products in stages from the first to the second and to the third reactive distillation column.

DESCRIPTION OF THE PREFERRED EMBODIMENTS

Figure 1:
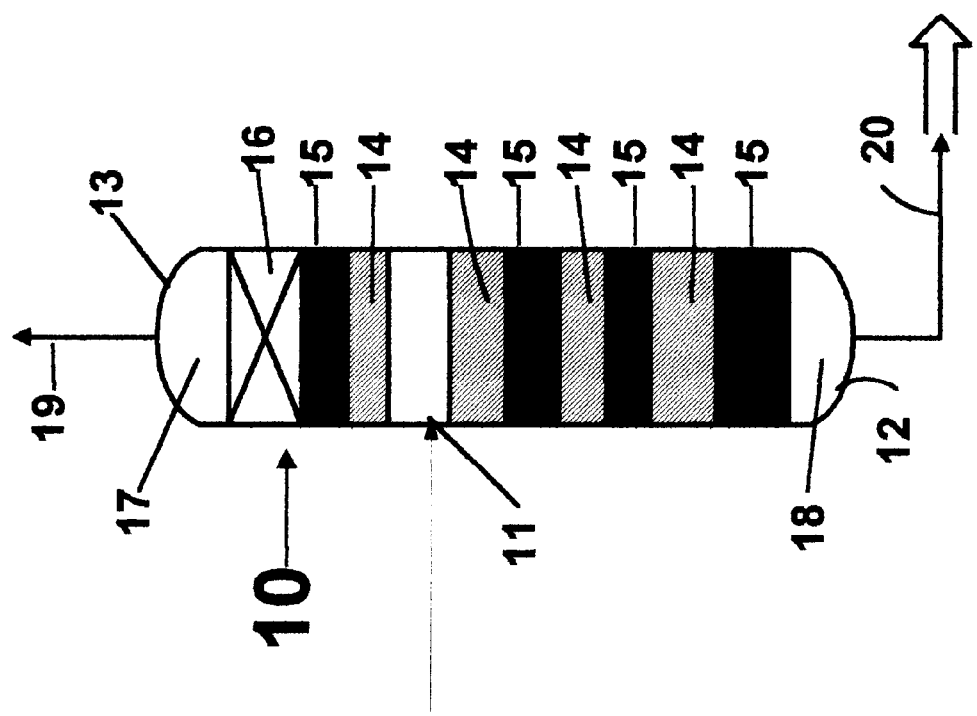
FIG. 1 is a diagrammatic drawing of a reactive distillation column used with the process of this invention utilizing a narrow range of lighter olefin-containing hydrocarbon feed stock of $C_5$ and higher carbon numbers being fed into the reactive distillation column at a predetermined point and with isomerizing catalyst near the predetermined feed point and disproportionating catalyst in place and in alternating arrangement with the isomerizing catalyst and with at least one vapor/liquid zone created at the top of the reactive distillation column for producing $C_6$ through $C_{10}$ carbon number olefins.

The present invention relates to a process for improving the yields of heavier olefins by using a substantially narrow range of lighter olefin-containing hydrocarbon feed stock, which is fed into a reaction distillation column, generally referred to at reference numeral 10. In at least one embodiment as shown in FIG. 1, the process of this invention commences with the feeding of the substantially narrow range of lighter olefin-containing hydrocarbon feed stock from $C_6$ and heavier carbon numbers into the reaction distillation column 10 at a predetermined point 11 in the reaction distillation column 10. Located near the predetermined point of feed 11 is an isomerization catalyst 14 for isomerizing the olefin-containing hydrocarbon feed stock as it is passed into the reactive distillation column 10. As shown in FIG. 1 the isomerization catalyst 14 would be located both near the predetermined feed point 11 and directly above and below the predetermined feed point 11 for first isomerizing the olefin-containing hydrocarbon feed stock as completely as possible. Thus in this preferred embodiment the predetermined feed point 11 would be located on the reactive distillation column for first directly feeding the olefin-containing hydrocarbon feedstock into the reactive distillation column 10 between the isomerization catalysts 14. Isomerizing the olefin, as those skilled in the art will know, means that the double bonds between the carbon atoms, which characterize an olefin, are moved from one pair of carbon atoms to another pair of carbon atoms with the purpose of creating predominantly an olefin molecule, which is not symmetrical, provided the olefin molecule has 5 or more carbon atoms. Once the olefin-containing hydrocarbon feed stock has been isomerized, it is then allowed to flow to a disproportionation catalyst 15 for disproportionating of the now isomerized olefin-containing hydrocarbon feed stock. In this preferred embodiment a disproportionating catalyst 15 would be located above and below the isomerization catalysts 14. This arrangement of catalysts may be either in separate trays or as molecular mixtures of the catalysts, which are created in admixture thereof. Disproportionating the olefin, as those skilled in the art will know, means that a splitting process occurs at the point of the olefinic bond on the olefin-containing hydrocarbon and a re-combining of the split parts with other split parts from other olefins which are being disproportionated at the same time to create both larger olefins and smaller olefins. In this preferred embodiment by having the disproportionation catalyst 15 located above and below the isomerizing catalysts 14 the olefins are as soon as they are isomerized move to be disproportionated in the reaction distillation column, as shown in FIG. 1.

Further as shown in FIG. 1, at least in this embodiment, there are provided alternating process steps of disproportionating and isomerizing of the olefin-containing hydrocarbon feed stock after its initial feed into the predetermined feed point 11 of the reaction distillation column 10 and its first isomerization. This alternating of the process steps of disproportionating and isomerizing said olefin-containing hydrocarbon feed stock will continue depending on the size of the reaction distillation column 10, but will generally have as it last process step a disproportionating step before reaching the bottoms 18 of the reaction distillation column 10.

As those skilled in the art will appreciate there are many catalysts and ways to prepare them in a reaction distillation column 10, but in this preferred embodiment, the disproportionation catalysts are selected from the groups of molybdenum, tungsten, cobalt, and rhenium metals and their oxides either individually or as combinations thereof and supported on porous substrates. For example in a preferred embodiment the disproportionation catalyst selected from a group of heavy metals is used which contains tungsten or rhenium oxides on a porous alumina or silica-containing supports. The porous alumina or silica-containing support used in this embodiment is catalytic grade gamma-alumina or silica-alumina, but any other substrate which would be effective to make the catalysts available for reaction with the olefins may be used and not depart from the teachings of this invention.

Some of the conventional methods of preparing the disproportionation catalyst mixture includes dry mixing, impregnation or co-precipitation. In one of the preferred embodiments a solution containing aqueous salts of rhenium or rhenium oxide and/or tungsten or tungsten oxide is prepared. Once prepared it is added to an alumina support which can be in the form of conventional dumped distillation packing, such as, saddles, rings, spheres to enhance mass transfer and reactive surface during disproportionating and fractionation or separation to the extent the operating parameters are appropriate. After impregnations, the catalyst would be calcined at 300 degrees Centigrade to 700 degrees Centigrade in the flow of air and/or nitrogen to activate the catalyst. In one preferred embodiment the disproportionation catalyst contained 5 to 20% by weight rhenium or 5 to 35% tungsten.

Also as those skilled in the art will appreciate there are many catalysts and ways to prepare isomerization catalyst for the reaction distillation column 10, but in this preferred embodiment the isomerization catalysts are selected from the groups of alkali metals such as sodium, potassium, rubidium or cesium either individually or as combinations thereof and then supported on alumina support. For example, carbonates, chelates, hydroxides, alkoxylates and other compounds can be used as the catalysts as long as they can be decomposed to leave some form of metal oxides on the surface for reaction with the olefins. In a preferred embodiment the metals of potassium carbonate and/or potassium carboxylates may be used, but after they are impregnated on a surface, they would be activated by being calcined at 400 degrees Centigrade to 800 degrees Centigrade in the presence of air flow. In at least one embodiment the isomerization catalyst of an alkali metal on the alumnia substrate should be from 5 to 20% by weight.

Also shown in FIG. 1 of the reactive distillation column 10, a vapor/liquid contacting zone 16 is located in the upper part of the reactive distillation column 10 for providing a vapor/liquid contacting zone for separation of the lighter reaction products from the heavier olefin-containing hydrocarbon feed stock. This vapor/liquid contacting zone 16 may consist as shown in this embodiment of several stages of structured packing or trays located in the upper most stages of the upper part 17 of the reaction distillation column 10. At this point the olefin-containing hydrocarbon feed stock has been both isomerized and disproportionated and olefin reaction products have been produced which are both heavier, lighter and approximately the same size as the feed stock. The advantage of providing at least one vapor/liquid zone 16 is that it improves the separation or fractionation of the lighter olefin reaction products from the heavier olefin reaction products produced from the olefin-containing hydrocarbon feedstock in the reaction distillation column 10. This is especially true at the top of the column, where reaction is inhibited by low temperatures and the light species are flashed off thus preventing their recombination with the other reactants. This removal of the light species thus shifts the equilibrium conversion of the feedstock toward heavier olefin-containing hydrocarbons. These light olefin reaction products are then removed by the overhead line 19 located in the top 13 of the reaction distillation column 10.

The process variables of temperature and pressure used in the reaction distillation column 10 to practice this invention will vary and depend on the olefin-containing hydrocarbon feedstock used, and the desired extent of reaction required to achieve the desired conversion and selectivity. In general, the temperature range will be between −50° degrees Fahrenheit to 200° degrees Fahrenheit at the top 13 where the lighter olefin reactant products are taken off by the overhead stream 19. At the bottom 12 in the reaction distillation column 10 where the heavier olefin reactant products are taken off by stream 20 from the bottoms 18 the temperature range will be between 200° degrees Fahrenheit to 600° degrees Fahrenheit. The pressures, in general will range from −14.5 PSIG to 250 PSIG but will also be varied by the required process temperature to achieve the desired conversion and selectivity of the desired olefin product. These process variables will require those skilled in the art who practice this invention to do some experimentation within these variables and within the ranges set out herein to maximize their results because these variables are dependant on the olefin-containing hydrocarbon feedstock and the desired product ranges. How these process variables may be adjusted will become more clear to those skilled in the art from the following examples herein set out and disclosed.

In example 1, using the schematic drawing of FIG. 1, a substantially narrow range of lighter olefin-containing hydrocarbon feed stock composed of a mixture, which is substantially $C_5$, $C_6$, and heavier, was fed into the reactive distillation column 10, at the predetermined feed point 11. It was isomerized and disproportionated by the isomerization catalyst 14 and the disproportionation catalyst 15 respectively and then alternatively treated by the respective catalysts thereafter. The process variables used in this example were: 20 PSIG, + or −10 PSI and a temperature of 40° degrees Fahrenheit, + or −40° degrees Fahrenheit at the top 13. At the bottoms 18 in the bottom 12 of the reaction distillation column 10 the variables were held at 400° degrees Fahrenheit + or −100° degrees Fahrenheit. Operated at these temperature and pressure variables the resultant product collected at the bottoms 18 for removal as desired heavier olefins would be a composition in the wt % as follows:

| | |
|---|---|
| $C_6$ | 3.1 |
| $C_7$ | 18.3 |
| $C_8$ | 61.7 |
| $C_9$ | 13.2 |
| $C_{10}$ | 2.5 |
| $C_{11}$ | 1.1 | thus producing a heavier olefins of substantially from $C_6$ through $C_{10}$.

In an example 2, using the schematic drawing of FIG. 1, a substantially narrow range of lighter olefin-containing hydrocarbon feed stock composed of a mixture which is substantially $C_5$, $C_6$, and heavier was fed into the reactive distillation column 10, in FIG. 1, at the predetermined feed point 11. It was immediately isomerized and disproportionated by the isomerization catalyst 14 and the disproportionation catalyst 15 and then alternatively treated by the respective catalyst thereafter. The process variables used with this example were: 20 PSIG + or −10 PSI and temperatures of 40° degrees Fahrenheit + or −40° degrees Fahrenheit at the top 13, while the bottom 12 of the reaction distillation column 10, and re-boiler temperature were held at 350° degrees Fahrenheit + or −100° degrees Fahrenheit. Operated at these temperature and pressure variables the resultant product collected at the bottoms 18 for removal as desired heavier olefins would be a composition in the wt % as follows:

| | |
|---|---|
| $C_5$ | 4.7 |
| $C_6$ | 38.5 |
| $C_7$ | 38.2 |
| $C_8$ | 18.6 | thus producing a slightly different heavier olefins of substantially from $C_6$ through $C_{10}$.

Figure 2:
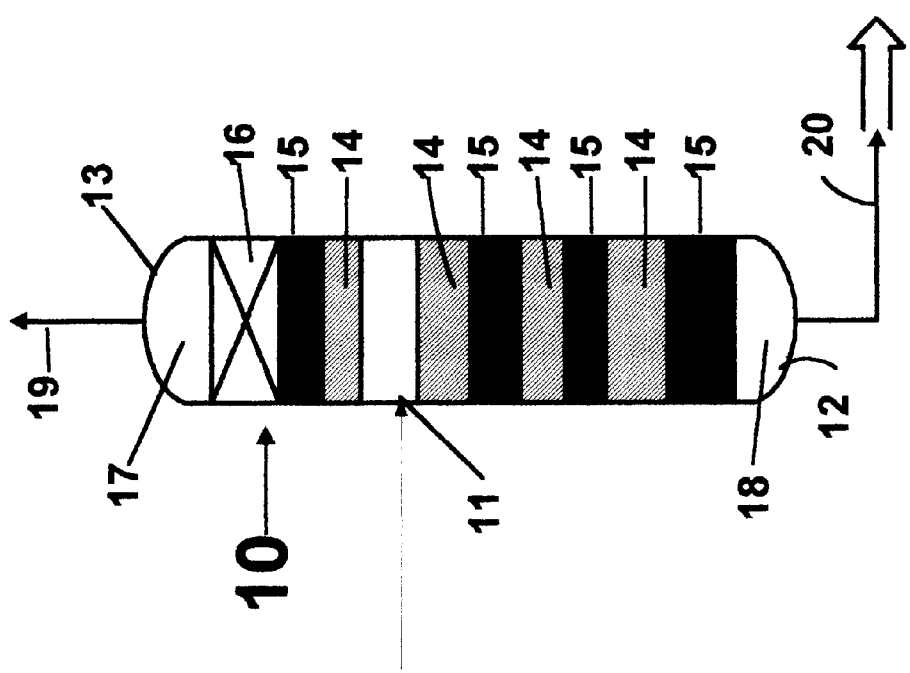
FIG. 2 is a diagrammatic drawing of a reactive distillation column used with the process of this invention utilizing a narrow range of lighter olefin-containing hydrocarbon feed stock of $C_6$ through $C_{10}$ and higher carbon numbers being fed into the reactive distillation column at a predetermined point and with isomerizing catalyst near the predetermined feed point and disproportionating catalyst in place and in alternating arrangement with the isomerizing catalyst and with at least one vapor/liquid zone created at the top of the reactive distillation column for producing C10 and higher carbon number olefins.

In an example 3, using the schematic drawing of FIG. 2, a substantially narrow range of lighter olefin-containing hydrocarbon feed stock composed of a mixture which is substantially $C_5$, through $C_{10}$, and heavier was fed into the reactive distillation column 10 at the feed point 11. It was immediately isomerized and disproportionated by the isomerization catalyst 14 and the disproportionation catalyst 15 and then alternatively treated by the respective catalyst therefore. The process variables used with this example were: 10 PSIG + or −10 PSI and a temperature of 40° degrees Fahrenheit + or −40 degrees Fahrenheit at the top 13 while the bottom 12 of the reaction distillation column 10, and a re-boiler temperature were held at 400° degrees Fahrenheit + or −100° degrees Fahrenheit. Operated at these temperature and pressure variables the resultant product collected at the bottoms 18 for removal as desired heavier olefins would be a composition in the wt % as follows:

| | |
|---|---|
| $C_8$ | 3.77 |
| $C_9$ | 20.16 |
| $C_{10}$ | 34.97 |
| $C_{11}$ | 25.1 |
| $C_{12}$ | 10.37 |
| $C_{13}$ | 3.87 |
| $C_{14}$ | 2.16 |
| $C_{15}$ | 0.59 | thus producing a slightly different heavier olefins of substantially from $C_{10}$ through $C_{20}$.

In an example 4, using the schematic drawing of FIG. 2, a substantially narrow range of lighter olefin-containing hydrocarbon feed stock composed of a mixture which is substantially $C_5$, through $C_{10}$, and heavier was feed into the reactive distillation column 10, in FIG. 2, at the predetermined feed point 11. It was immediately isomerized and disproportionated by the isomerization catalyst 14 and the disproportionation catalyst 15 and then alternatively treated by the respective catalyst thereafter. The process variables used with this example were: at the top 13 of the column generally 10 PSIG + or −10 PSI and a temperature of 40° degrees Fahrenheit + or −40° degrees Fahrenheit while the bottom 12 of the reaction distillation column 10, where a re-boiler would be located, would be 450° degrees Fahrenheit + or −100° degrees Fahrenheit. Operated at these temperature and pressure variables the resultant product collected at the bottoms 18 for removal as desired heavier olefins would be a composition in the wt % as follows:

| | |
|---|---|
| $C_7$ | 0.2 |
| $C_8$ | 1.0 |
| $C_9$ | 6.6 |
| $C_{10}$ | 16.4 |
| $C_{11}$ | 23.5 |
| $C_{12}$ | 21.4 |
| $C_{13}$ | 14.3 |

| | |
|---|---|
| $C_{14}$ | 8.3 |
| $C_{15}$ | 4.2 |
| $C_{16}$ | 2.0 |
| $C_{17}$ | 0.9 |
| $C_{18}$ | 0.4 | thus producing a slightly different heavier olefins of substantially from $C_{10}$ through $C_{20}$.

The yield in this process to heavy products ($C_6$ and heavier) is thought to be in the range of 20% to 80% by weight, more preferably 50% to 75% by weight. Most preferably, the yield to heavy products will be about 70% by weight. As shown above the product distribution can be controlled or modified by varying temperatures and pressure variables in the reaction distillation column.

In at least another embodiment of this invention as shown in FIG. 3, the process of this invention commences with the feeding of a substantially narrow range of lighter olefin-containing hydrocarbon feed stock from $C_3$ to $C_4$, with $C_4$ being composed at least partially of 1- and 2-butene, into the reaction distillation column 10 at a predetermined point 11 between the bottom 12 and the top 13 of the reaction distillation column 10. In this embodiment the resultant products are ethylene, propylene and some 2-butene which will be taken out by the overhead line or stream 19 off the top 13 of the reaction distillation column 10 and $C_5$ through $C_{10}$ which will be taken from the bottoms 18 of the bottom 12 of the reaction distillation column 10 by a line 20. In this embodiment a disproportionation catalyst 15 for disproportionating the olefin-containing hydrocarbon feed stock as it is passed into the reactive distillation column 10, is provided and located near the predetermined point of feed 11. As shown in FIG. 3 the disproportionating catalyst 15 would be located both near the predetermined feed point 11 and directly above and below the feed point 11 for first disproportionating the olefin-containing hydrocarbon feed stock as completely as possible. Thus in this preferred embodiment the predetermined feed point 11 would be located on the reactive distillation column 10 for first directly feeding the olefin-containing hydrocarbon feedstock into the reactive distillation column 10 between the disproportionation catalyst 15. Once the olefin-containing hydrocarbon feed stock has been disproportionated, it is then allowed to flow to an isomerization catalyst 14 for isomerization of the now disproportionated olefin-containing hydrocarbon feed stock. In this preferred embodiment disclosed an isomerization catalyst 14 would be located above and below the disproportionation catalyst 15 for isomerizing the reaction product from the disproportionation catalyst 15. The disproportionating catalyst 15 is located for first reacting the olefin-containing feedstock in this embodiment for at least the reason that the feedstock of $C_3$ and $C_4$, with $C_4$ being composed of 1- and 2-butenes, which can only be isomerized to predominantly 2-butene and that yields only 2-butene when it is disproportionated by the disproportionation catalyst 15. After the feed stock is first disproportionated by the disproportionation catalyst 15, some of the resultant reactant products have a molecular size and symmetry for which isomerization by the isomerization catalyst 14 has a purpose and the other reactant products are smaller molecules which are then removed into the vapor phase by separation or fractionation of these lighter olefin and other light reaction products from the heavier olefin reaction products in the reaction distillation column 10. In the embodiment of FIG. 3, there is then provided alternation of the process steps of disproportionating and isomerizing after this initial stage of disproportionation, wherein disproportionation and isomerization process steps are continued in the reaction distillation column 10 and finally ending in a disproportionation process step before the resultant products of $C_5$ through $C_{10}$ will be delivered into the bottoms 18 at the bottom 12 of the reaction distillation column 10.

The process variables using the schematic drawing shown in FIG. 3 but with an example 5 using the narrow range of lighter olefin-containing hydrocarbon feed stock made from $C_3$ and $C_4$ olefins and the process variables being at the top 13 of the reactive distillation column 10 generally in the 100 PSIG, + or −80 PSI and a temperature of 100° Degrees Fahrenheit, + or −50° degrees Fahrenheit while the bottom 12 of the reaction distillation column 10, where a re-boiler would be located, would be 300° degrees Fahrenheit + or −100° degrees Fahrenheit. Operated at these temperature and pressure variables the resultant product collected at the bottoms 18 for removal as desired heavier olefins would be a composition in the wt % as follows:

| | |
|---|---|
| $C_4$ | 8.15 |
| $C_5$ | 46.21 |
| $C_6$ | 26.92 |
| $C_7$ | 13.31 |
| $C_8$ | 1.69 | thus producing a heavier olefin of substantially from $C_5$ through $C_{10}$.

As those skilled in art will appreciate these process methods above disclosed could be practiced all in one reaction distillation column or in a series of columns as shown in FIG. 4 to take a lighter olefin-containing hydrocarbon from $C_3$ to $C_4$ to heavier olefin-containing hydrocarbon of substantially $C_{14}$ and heavier product without departing from the teachings of this invention. Obviously if all the process methods were combined into one reaction distillation column the variables for each stage would have to be maintained and the look of the reaction distillation columns 10, as shown would have a different structure, but the process methods would be the same equivalent processes. In FIG. 4 a serial process using multiple columns is shown with the first stage being generally shown at reference number 21, which is generally the process of FIG. 3, the second stage is generally shown at reference number 22, which is generally the process of FIG. 1, and the third stage is generally shown at reference number 23, which is generally the process of FIG. 2.

Also as those skilled in the art should appreciate these process methods above disclosed while run with linear olefins, they could also have been run with branched chain olefin-containing hydrocarbons or as a mixed process with both linear and branched chain olefins. In the case were a specific percent mixture of branched chain olefins with the linear olefin would be desired, then the feedstock mixture of the branched chain olefin-containing hydrocarbon feedstock would be adjusted with the linear olefin-containing hydrocarbon feedstock to achieve the desired percentage of the branched olefin in the resultant products produced by the process methods of this invention.

While the preferred embodiments of the intention of this process and their operational use have been described for the improved yields of heavier olefins from substantially narrow range of lighter olefin-containing hydrocarbon feed stock in a reactive distillation column, it will be appreciated that other embodiments and process variables may be used without departing from the spirit of the invention of this process here in claimed.

I claim:

1. A process for improved yields of heavier olefins from a substantially narrow range of lighter olefin-containing-hydrocarbon-feed stock in a reactive distillation column comprising;
   feeding a substantially narrow range of lighter olefin-containing hydrocarbon feed stock of at least $C_5$ to higher carbon numbers into a reaction distillation column at a predetermined point in said reactive distillation column,
   first isomerizing said lighter olefin-containing hydrocarbon feed stock with an isomerization catalyst near said predetermined point of feeding said substantially narrow range of lighter olefin-containing hydrocarbon feed stock into said reactive distillation column,
   second disproportinating said lighter olefin-containing hydrocarbon feed stock, which has been isomerized, with a disproportionation catalyst into heavier and lighter olefin-containing hydrocarbons in said reactive distillation column,
   providing at least one vapor/liquid contacting zone for improved separation of said heavier and lighter olefin-containing hydrocarbons,
   maintaining a pressure in said reactive distillation column for allowing a sufficiently high recovery of the lowest molecular weight olefins of said heavier molecular weight olefins in the bottom of said reactive distillation column, and for allowing a high conversion of lighter olefin-containing hydrocarbon feed stock,
   maintaining a temperature at the top of said reaction distillation column sufficient to remove the heaviest of said light molecular weight olefins overhead from said reactive distillation column, and
   maintaining a temperature in said bottom of said reactive distillation column sufficient for allowing recovery of the lightest of said higher molecular weight olefins in said bottom of said reactive distillation column and for maintaining an adequate temperature profile in said reactive distillation column for allowing sufficiently high reaction rates throughout said reactive distillation column.

2. The process for improved yields of heavier olefins from a substantially narrow range of lighter olefin-containing hydrocarbon feed stock in a reactive distillation column of claim 1 further comprising;
   alternating the process steps of disproportionating and isomerizing said lighter olefin-containing hydrocarbon feed stock.

3. The process for improved yields of heavier olefins from a substantially narrow range of lighter olefin-containing hydrocarbon feed stock in a reactive distillation column of claim 2 wherein said vapor/liquid contacting zone for separation of said heavier and lighter olefins comprises;
   positioning said at least one vapor/liquid contacting zone in said reactive distillation column for improving separation of said light olefins as vapor phase overhead and said heavier olefins as liquid phase bottoms in said reactive distillation column.

4. The process for improved yields of heavier olefins from a substantially narrow range of lighter olefin-containing hydrocarbon feed stock in a reactive distillation column of claim 3 wherein said alternating isomerizing and disproportionating of said lighter olefin-containing hydrocarbon feed stock further comprises;
   providing said isomerizing and disproportionating catalysts in alternating quantities in said reactive distillation column.

5. The process for improved yields of heavier olefins from a substantially narrow range of lighter olefin-containing hydrocarbon feed stock in a reactive distillation column of claim 4 wherein said providing of said isomerizing and disproportionating catalysts in alternating quantities to said reactive distillation column further comprises;
   providing said isomerizing and disproportionating catalysts in alternating beds in said reactive distillation column.

6. The process for improved yields of heavier olefins from a substantially narrow range of lighter olefin-containing hydrocarbon feed stock in a reactive distillation column of claim 5 wherein said isomerization catalyst comprising a metal selected from the group consisting of sodium, potassium, rubidium, and cesium impregnated on a substrate.

7. The process for improved yields of heavier olefins from a substantially narrow range of lighter olefin-containing hydrocarbon feed stock in a reactive distillation column of claim 6 wherein said isomerization catalyst comprising of a metal further comprising metals selected from the group consisting of sodium, potassium, rubidium, cesium and mixtures thereof impregnated on a substrate.

8. The process for improved yields of heavier olefins from a substantially narrow range of lighter olefin-containing hydrocarbon feed stock in a reactive distillation column of claim 7 wherein said disproportionation catalyst comprising a heavy metal selected from the group consisting of rhenium, tungsten, and molybdenum, impregnated on a substrate.

9. The process for improved yields of heavier olefins from a substantially narrow range of lighter olefin-containing hydrocarbon feed stock in a reactive distillation column of claim 8 wherein said disproportionation catalyst comprising a heavy metals selected from the group consisting of rhenium, tungsten, molybdenum, and mixtures thereof, impregnated on a substrate.

10. The process for improved yields of heavier olefins from a substantially narrow range of lighter olefin-containing hydrocarbon feed stock in a reactive distillation column of claim 9 wherein said feed of said substantially narrow range of lighter olefin-containing hydrocarbon feed stock comprises;
    feeding a mixture of substantially $C_5$, $C_6$ and heavier olefin-containing hydrocarbon feed stock into said reactive distillation column at said predetermined point in said reactive distillation column.

11. The process for improved yields of heavier olefins from a substantially narrow range of lighter olefin-containing hydrocarbon feed stock in a reactive distillation column of claim 10 wherein said maintained pressure in f said reactive distillation column comprises;
    maintaining said pressure in the top of said reactive distillation column with in a range of from −10 PSIG to 200 PSIG.

12. The process for improved yields of heavier olefins from a substantially narrow range of lighter olefin-containing hydrocarbon feed stock in a reactive distillation column of claim 11 wherein said maintained pressure at said top of said reactive distillation column comprises;
    maintaining said pressure at said top of said reactive distillation column with in a range of from 5 PSIG to 125 PSIG.

13. The process for improved yields of heavier olefins from a substantially narrow range of lighter olefin-containing hydrocarbon feed stock in a reactive distillation column of claim 12 further comprising;
- maintaining said temperature in said bottom of said reactive distillation column within a range of from 100° F. to 500° F., and
- maintaining said temperature at said top of said reactive distillation column within a range of from 0° F. to 300° F.

14. The process for improved yields of heavier olefins from a substantially narrow range of lighter olefin-containing hydrocarbon feed stock in a reactive distillation column of claim 13 wherein said feeding of lighter olefin-containing hydrocarbon feedstock of substantially $C_5$, $C_6$ and heavier carbon numbers further comprises;
- producing heavier olefins of substantially from $C_6$ through $C_{10}$ at yields of at least 60% by weight.

15. The process for improved yields of heavier olefins from a substantially narrow range of lighter olefin-containing hydrocarbon feed stock in a reactive distillation column of claim 9 wherein said feed substantially narrow range of lighter olefin-containing hydrocarbon feed stock comprises;
- feeding a mixture of substantially $C_6$ through $C_{10}$ into a reactive distillation column at said predetermined point in said reactive distillation column.

16. The process for improved yields of heavier olefins from a substantially narrow range of lighter olefin-containing hydrocarbon feed stock in a reactive distillation column of claim 15 wherein said maintained pressure at said top of said reactive distillation column comprises;
- maintaining said pressure at said top of said reactive distillation column with in a range of from −10 PSIG to 200 PSIG.

17. The process for improved yields of heavier olefins from a substantially narrow range of lighter olefin-containing hydrocarbon feed stock in a reactive distillation column of claim 16 wherein said maintained pressure at said top of said reactive distillation column comprises;
- maintaining said pressure at said top of said reactive distillation column with in a range of from 5 PSIG to 75 PSIG.

18. The process for improved yields of heavier olefins from a substantially narrow range of lighter olefin-containing hydrocarbon feed stock in a reactive distillation column of claim 17 further comprising;
- maintaining said temperature at said bottom of said reactive distillation column with in a range of from 100° F. to 500° F. and
- maintaining said temperature at said top of said reactive distillation column within a range of from 0° F. to 300° F.

19. The process for improved yields of heavier olefins from a substantially narrow range of lighter olefin-containing hydrocarbon feed stock in a reactive distillation column of claim 18 wherein said feeding of lighter olefin-containing hydrocarbon feed stock of from $C_6$ through $C_{10}$ further comprises;
- producing heavier olefin-containing hydrocarbons of substantially from $C_{10}$ through $C_{20}$ at yields of at least 55% by weight.

20. The process for improved yields of heavier olefins from a substantially narrow range of lighter olefin-containing hydrocarbon feed stock in a reactive distillation column of claim 9 wherein said feed of said substantially narrow range of lighter olefin-containing hydrocarbon feed stock comprises:
- feeding a feed stock mixture of substantially $C_{10}$ through $C_{20}$ olefin-containing hydrocarbon feed stock into said reactive distillation column at said predetermined point in said reactive distillation column.

21. The process for improved yields of heavier olefins from a substantially narrow range of lighter olefin-containing hydrocarbon feed stock in a reactive distillation column of claim 20 wherein said maintained pressure at said top of said reactive distillation column comprises;
- maintaining said pressure at said top of said reactive distillation column with in a range of from −14.5 PSIG to 50.0 PSIG.

22. The process for improved yields of heavier olefins from a substantially narrow range of lighter olefin-containing hydrocarbon feed stock in a reactive distillation column of claim 21 wherein said maintained pressure at said top of said reactive distillation column comprises;
- maintaining said pressure at said top of said reactive distillation column with in a range of from −10.0 PSIG to 5.00 PSIG.

23. The process for improved yields of heavier olefins from a substantially narrow range of lighter olefin-containing hydrocarbon feed stock in a reactive distillation column of claim 22 further comprising;
- maintaining said temperature at said bottom of said reactive distillation column with in a range of from 100° F. to 500° F., and
- maintaining said temperature at said top of said reactive distillation column within a range of from 0° F. to 300° F.

24. The process for improved yields of heavier olefins from a substantially narrow range of lighter olefin-containing hydrocarbon feed stock in a reactive distillation column of claim 23 wherein said feeding of olefin-containing hydrocarbon feed stock of $C_{10}$ through $C_{20}$ further comprises;
- producing heavier olefin hydrocarbons of substantially $C_{14}$ and heavier product at yields of at least 53% by weight.

25. A process for improved yields of heavier olefins from a substantially narrow range of lighter olefin-containing hydrocarbon feed stock in a reactive distillation column comprising;
- feeding a substantially narrow range of lighter olefin-containing hydrocarbon feed stock of at least $C_3$ and $C_4$ to heavier into a reaction distillation column at a predetermined point in said reactive distillation column,
- first disproportionating said at least $C_3$ and $C_4$ to heavier range of olefin-containing hydrocarbon feed, stock with a disproportionating catalyst into heavier and lighter olefin-containing hydrocarbons near said predetermined point of feeding said substantially narrow range of lighter olefin-containing hydrocarbon feed stock of at least $C_3$ and $C_4$ to heavier into said reaction distillation column,
- second isomerizing said products of disproportionation of said at least $C_3$ and $C_4$ to heavier range of olefin-containing hydrocarbon feed stock with an isomerizing catalyst in said reaction distillation column,
- providing at least one vapor/liquid contacting zone for improved separation of said heaver and lighter olefin-containing hydrocarbons,
- maintaining a pressure in said reactive distillation column for allowing a sufficiently high recovery of the lowest molecular weight olefin of said heavier molecular weight olefins in the bottom of said reaction distillation column, and for allowing a high conversion rate of said narrow range of lighter olefin-containing hydrocarbon feed stock, maintaining a temperature at the top of said reaction distillation column sufficient for removing the heaviest of said light molecular weight olefins overhead from said reaction distillation column, and maintaining a in said bottom of the reactive distillation column sufficient for allowing recovery of the lightest of said higher molecular weight olefins in said bottom of said reactive distillation column and for maintaining an adequate temperature profile in said reactive distillation column for allowing sufficiently high reaction rates throughout said reactive distillation column.

26. The process for improved yields of heavier olefins from a substantially narrow range of lighter olefin-containing hydrocarbon feed stock in a reactive distillation column of claim 25 further comprising;

alternating the process steps of disproportionating and isomerizing said products of disproportionation of said lighter olefin-containing hydrocarbon feed stock.

27. The process for improved yields of heavier olefins from a substantially narrow range of lighter olefin-containing hydrocarbon feed stock in a reactive distillation column of claim 26 further comprising;

positioning said at least one vapor/liquid contacting zone in said reactive distillation column for separating said lighter olefins as vapor phase and said heavier olefins as liquid phase.

28. The process for improved yields of heavier olefins from a substantially narrow range of lighter olefin-containing hydrocarbon feed stock in a reactive distillation column of claim 27 wherein said alternating disproportionating and isomerizing said lighter olefin-containing hydrocarbon feed stock further comprises;

providing said disproportionating and isomerizing catalysts in alternating quantities in said reactive distillation column.

29. The process for improved yields of heavier olefins from a substantially narrow range of lighter olefin-containing hydrocarbon feed stock in a reactive distillation column of claim 28 wherein said providing said disproportionating and isomerizing catalysts in alternating quantities to said reactive distillation column further comprises;

providing said disproportionating and isomerizing catalysts on alternating beds in said reactive distillation column.

30. The process for improved yields of heavier olefins from a substantially narrow range of lighter olefin-containing hydrocarbon feed stock in a reactive distillation column of claim 29 wherein said isomerization catalyst comprising a metal selected from t he group consisting of sodium, potassium, rubidium, and cesium impregnated on a substrate.

31. The process for improved yields of heavier olefins from a substantially narrow range of lighter olefin-containing hydrocarbon feed stock in a reactive distillation column of claim 30 wherein said isomerization catalyst comprising a metal selected from the group consisting of sodium, potassium, rubidium, and cesium further comprising metals selected from the group consisting of sodium, potassium, rubidium, cesium, and mixtures thereof impregnated on a substrate.

32. The process for improved yields of heavier olefins from a substantially narrow range of lighter olefin-containing hydrocarbon feed stock in a reactive distillation column of claim 31 wherein said disproportionation catalyst comprising a heavy metal selected from the group consisting of rhenium, tungsten and molybdenum impregnated on a substrate.

33. The process for improved yields of heavier olefins from a substantially narrow range of lighter olefin-containing hydrocarbon feed stock in a reactive distillation column of claim 32 wherein said isomerization catalyst consisting of heavy metal selected from the group consisting of rhenium, tungsten and molybdenum comprising metals selected from the group consisting of rhenium, tungsten, molybdenum and mixtures thereof impregnated on a substrate.

34. The process for improved yields of heavier olefins from a substantially narrow range of lighter olefin-containing hydrocarbon feed stock in a reactive distillation column claim 33 wherein said maintained pressure at said top of said reactive distillation column comprises;

maintaining said pressure in said top of said reactive distillation column with in a range of from 0 PSIG to 500 PSIG.

35. The process for improved yields of heavier olefins from a substantially narrow range of lighter olefin-containing hydrocarbon feed stock in a reactive distillation column of claim 34 wherein said maintained pressure at said top of said reactive distillation column comprises;

maintaining said pressure at said top of said reactive distillation column with in a range of from 80 PSIG to 200 PSIG.

36. The process for improved yields of heavier olefins from a substantially narrow range of lighter olefin-containing hydrocarbon feed stock in a reactive distillation column of claim 35 further comprising;

maintaining temperature at said bottom of said reactive distillation column within a range of from 100° F. to 500° F., and maintaining said temperature at said top of said reactive distillation column within a range of from −50° F. to 300° F.

37. The process for improved yields of heavier olefins from a substantially narrow range of lighter olefin-containing hydrocarbon feed stock in a reactive distillation column of claim 36 wherein said olefin-containing hydrocarbon feed stock of from $C_3$ and $C_4$ further comprises;

producing heavier olefin-containing hydrocarbons of substantially from $C_5$ through $C_{10}$ at yields of at least 63% by weight.

38. The process for improved yields of heavier olefins from a substantially narrow range of lighter olefin-containing hydrocarbon feed stock in a reactive distillation column of claim 10 wherein said feed of said substantially narrow range of lighter olefin-containing hydrocarbon feed stock comprises;

feeding measured amounts of specifically branched olefin-containing hydrocarbons for making the desired amount of branching in the desired heavier product to be from essentially 0% branched molecules to essentially 100% branched molecules on the average of said heavier olefin products.

39. The process for improved yields of heavier olefins from a substantially narrow range of lighter olefin-containing hydrocarbon feed stock in a reactive distillation column of claim 15 wherein said feed of said substantially narrow range of lighter olefin-containing hydrocarbon feed stock comprises;

feeding measured amounts of specifically branched olefin-containing hydrocarbons for making the desired amount of branching in the desired heavier olefin product to be from essentially 0% branched molecules to essentially 100% branched molecules on the average of said heavier olefin products.

40. The process for improved yields of heavier olefins from a substantially narrow range of lighter olefin-containing hydrocarbon feed stock mixture in a reactive distillation column of claim 20 wherein said feed of said substantially narrow range of lighter olefin-containing hydrocarbon feed stock comprises;

feeding measured amounts of specifically branched olefin-containing hydrocarbons for making the desired amount of branching in the desired heavier olefin products to be from essentially 0% branched molecules to essentially 100% branched molecules on the average of said heavier olefin products.

41. The process for improved yields of heavier olefins from a substantially narrow range of lighter olefin-containing hydrocarbon feed stock in a reactive distillation column of claim 25 wherein said feed of said substantially narrow range of lighter olefin-containing hydrocarbon feed stock comprises;

feeding measured amounts of specifically branched olefin-containing hydrocarbons for making the desired amount of branching in the desired heavier products to be from essentially 0% branched molecules to essentially 100% branched molecules on the average of said heavier olefin products.

* * * * *